US010289201B2

(12) United States Patent
Cruz-Hernandez

(10) Patent No.: US 10,289,201 B2
(45) Date of Patent: May 14, 2019

(54) METHOD AND APPARATUS FOR GENERATING MOOD-BASED HAPTIC FEEDBACK

(71) Applicant: Immersion Corporation, San Jose, CA (US)

(72) Inventor: Juan Manuel Cruz-Hernandez, Montreal (CA)

(73) Assignee: Immersion Corporation, San Jose, CA (US)

(*) Notice: Subject to any disclaimer, the term of this patent is extended or adjusted under 35 U.S.C. 154(b) by 14 days.

(21) Appl. No.: 15/822,649

(22) Filed: Nov. 27, 2017

(65) Prior Publication Data

US 2018/0143692 A1 May 24, 2018

Related U.S. Application Data

(63) Continuation of application No. 13/765,417, filed on Feb. 12, 2013, now Pat. No. 9,841,816, which is a
(Continued)

(51) Int. Cl.
*G06F 3/01* (2006.01)
*A61B 5/00* (2006.01)
(Continued)

(52) U.S. Cl.
CPC .......... *G06F 3/016* (2013.01); *A61B 5/02438* (2013.01); *A61B 5/165* (2013.01);
(Continued)

(58) Field of Classification Search
CPC ....................................................... G06F 3/016
(Continued)

(56) References Cited

U.S. PATENT DOCUMENTS 5,720,619 A * 2/1998 Fisslinger ............... A63F 13/10
434/336
6,190,314 B1 * 2/2001 Ark ........................ G06F 9/451
600/300
(Continued)

FOREIGN PATENT DOCUMENTS

GB 2 416 962 2/2006
JP 2001252265 A 9/2001
(Continued)

OTHER PUBLICATIONS

Brown, Lorna M. et al., "Shake2Talk: Multimodal Messaging for Interpersonal Communication", Nov. 29, 2007, Haptic and Audio Interaction Design; [Lecture Notes in Computer Science], Springer-Verlag Berlin Heidelberg 2007, pp. 44-55.
(Continued)

*Primary Examiner* — Eric Blount
(74) *Attorney, Agent, or Firm* — Miles & Stockbridge, P.C.

(57) ABSTRACT

A method and apparatus for generating mood-based haptic feedback are disclosed. A haptic system includes a sensing device, a digital processing unit, and a haptic generator. The sensing device, in one embodiment, is configured to detect user's modalities in accordance with mood information collected by one or more sensors and capable of issuing a sensing signal in response to the user's modalities. The digital processing unit is capable of identifying a user's condition in accordance with the sensing signal and providing a haptic signal in response to the user's condition. The user's condition, in one aspect, indicates user's mood and/or user's psychological conditions. The haptic generator generates haptic feedback in accordance with the haptic signal.

20 Claims, 6 Drawing Sheets

Related U.S. Application Data continuation of application No. 13/214,604, filed on Aug. 22, 2011, now Pat. No. 8,390,439, which is a continuation of application No. 12/274,152, filed on Nov. 19, 2008, now Pat. No. 8,004,391.

(51) Int. Cl.
 *A61B 5/16* (2006.01)
 *A61B 5/024* (2006.01)
 *G06F 17/30* (2006.01)

(52) U.S. Cl.
 CPC .......... *A61B 5/6898* (2013.01); *A61B 5/7455* (2013.01); *G06F 3/015* (2013.01); *G06F 17/30002* (2013.01); *A63F 2300/1012* (2013.01); *A63F 2300/6027* (2013.01); *G06F 2203/011* (2013.01); *H04M 2250/12* (2013.01)

(58) Field of Classification Search
 USPC .......................................... 340/573.1, 407.1
 See application file for complete search history.

(56) References Cited

U.S. PATENT DOCUMENTS

| | | | |
|---|---|---|---|
| 7,027,621 | B1 | 4/2006 | Prokoski |
| 7,148,789 | B2* | 12/2006 | Sadler .................... G06F 1/1626 340/407.1 |
| 7,493,365 | B2 | 2/2009 | Wies et al. |
| 7,698,238 | B2* | 4/2010 | Barletta .................. G06F 3/011 463/36 |
| 7,978,081 | B2 | 7/2011 | Shears et al. |
| 8,073,707 | B2 | 12/2011 | Teller et al. |
| 8,157,730 | B2 | 4/2012 | LeBoeuf et al. |
| 8,638,301 | B2 | 1/2014 | Birnbaum et al. |
| 9,046,884 | B2 | 6/2015 | Roseway et al. |
| 2004/0125120 | A1 | 7/2004 | Weiner |
| 2004/0229692 | A1 | 11/2004 | Breving |
| 2004/0242976 | A1* | 12/2004 | Abreu .................. A61B 5/0008 600/315 |
| 2006/0221935 | A1 | 10/2006 | Wong et al. |
| 2007/0033259 | A1* | 2/2007 | Wies .......................... G06F 3/01 709/206 |
| 2007/0063849 | A1* | 3/2007 | Rosella .................. A41D 1/002 340/573.1 |
| 2007/0135689 | A1 | 6/2007 | Asukai et al. |
| 2007/0149282 | A1 | 6/2007 | Lu et al. |
| 2008/0151038 | A1 | 6/2008 | Khouri et al. |
| 2008/0153554 | A1 | 6/2008 | Yoon et al. |
| 2008/0220865 | A1* | 9/2008 | Hsu .......................... A63F 13/08 463/37 |
| 2008/0287147 | A1* | 11/2008 | Grant ...................... G06F 1/1626 455/466 |
| 2008/0300055 | A1 | 12/2008 | Lutnick et al. |
| 2009/0002178 | A1 | 1/2009 | Guday et al. |
| 2009/0110246 | A1 | 4/2009 | Olsson et al. |
| 2010/0201500 | A1 | 8/2010 | Stirling et al. |

FOREIGN PATENT DOCUMENTS

| | | |
|---|---|---|
| JP | 2005152054 A | 6/2005 |
| JP | 2007115147 A | 5/2007 |
| WO | 2008144108 A1 | 11/2008 |
| WO | 2009002577 A1 | 12/2008 |

OTHER PUBLICATIONS

Chen, Chun-Yi et al., "ComSlipper: An Expressive Design to Support Awareness and Availability" ACM, 2 Penn Plaza, Suite 701, New York, USA, Apr. 22, 2006-Apr. 27, 2006, pp. 369-374.

Ciota, Zygmunt et al., "Audio-Haptic Feedback in Speech Processing," Haptic, Audio and Visual Environments and Games, 2007, HAVE 2007, IEEE International Workshop on IEEE, PI, Oct. 1, 2007, pp. 67-70.

Maclean, Karon E. et al., "Do it Yourself Haptics; Part II," IEEE Robotics & Automation Magazine, IEEE Service Center, Piscataway, NJ, US, vol. 14, No. 1, Mar. 1, 2008, pp. 104-119.

Mandryk, Regan L. et al., "A Continuous and Objective Evaluation of Emotional Experience with Interactive Play Environments," Proceedings of the Sigchi Conference on Human Factors in Computing, CHI 2006 Proceedings, Montreal, Quebec, Canada, Apr. 22, 2006-Apr. 27, 2006, pp. 1027-1036.

Nasoz, Fatma et al., "Multimodal Affective Driver Interfaces for Future Cars," ACM, 2 Penn Plaza, Suite 701, New York USA, Dec. 1, 2002-Dec. 6, 2002, pp. 319-322.

Unknown, "Haptics: Improving the Mobile User Experience through Touch," [online] Immersion Corporation, 2007. Retrieved from the internet: <URL: http://static.fiercemarkets.com/public/ads/immersion/haptics_improving-mobile-ue-through-touch.pdf>.

U.S. Appl. No. 13/765,417.

* cited by examiner

METHOD AND APPARATUS FOR GENERATING MOOD-BASED HAPTIC FEEDBACK

CROSS-REFERENCE TO RELATED APPLICATIONS

This application is a continuation application of U.S. patent application Ser. No. 13/765,417, filed Feb. 12, 2013, which is a continuation of U.S. patent application Ser. No. 13/214,604, filed on Aug. 22, 2011 and issued on Mar. 5, 2013 as U.S. Pat. No. 8,390,439, which is a continuation application of U.S. patent application Ser. No. 12/274,152, filed on Nov. 19, 2008 and issued on Aug. 23, 2011 as U.S. Pat. No. 8,004,391. The content of each of these applications is incorporated herein by reference.

FIELD

The exemplary embodiment(s) of the present invention relates to the field of electronic communications. More specifically, the exemplary embodiment(s) of the present invention relates to communications using haptic feedbacks.

BACKGROUND

As computer-based systems, appliances, automated teller machines (ATM), point of sale terminals and the like become more prevalent, the ease of use of the human-machine interface is becoming more important. Such interfaces should operate intuitively and require little or no user training whereby they can be used by virtually anyone. Many conventional user interface devices are available on the market, such as key boards, mouse, joysticks, and touch screens. One of the more intuitive and interactive interface devices known is the touch sensitive panel, which can be a touch screen or a touch pad. A touch screen includes a touch sensitive input panel and a display device, and provides a user with a machine interface through a panel sensitive to the user's touch and displaying content that the user can see and then "touch."

Conventional human-machine interfaces, such as keyboard, voice, and touch screen, typically require visual assistance or look during the interface operation. For instance, when a user inputs his or her selection(s) over a touch screen, the user needs to look and/or identify the location to be touched. Also, when a user operates a mouse, the user needs to see the movement of an icon on the screen before he or she can press the click button.

A problem associated with the conventional human-machine interfaces is that sometimes visual assistance is not available during the operation of human-machine interface. For example, a truck driver or a pilot often needs to keep his or her vision on driving or flying, and thus, cannot look at the interface device during an input/selection operation. Also, a worker may not be able to hear audible instructions in a noisy environment.

SUMMARY

The embodiment(s) of the present invention includes a haptic system capable of generating mood-based haptic feedback and method for making the same. A haptic system includes a sensing device, a digital processing unit, and a haptic generator. The sensing device, in one embodiment, is configured to detect user's modalities in accordance with mood information collected by one or more sensors and is capable of issuing a sensing signal in response to the user's modalities. The digital processing unit is capable of identifying a user's condition in accordance with the sensing signal and providing a haptic signal in response to the user's condition. The user's condition, in one aspect, indicates user's mood or user's psychological conditions. The haptic generator generates haptic feedback in accordance with the haptic signal.

Additional features and benefits of the exemplary embodiment(s) of the present invention will become apparent from the detailed description, figures and claims set forth below.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

Embodiments of the present invention are described herein in the context of a method, system and apparatus for providing mood-based haptic feedback in response to one or more events using a portable haptic device.

Those of ordinary skills in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the exemplary embodiments of the present invention as illustrated in the accompanying drawings. The same reference indicators (or numbers) will be used throughout the drawings and the following detailed description to refer to the same or like parts.

In the interest of clarity, not all of the standard hardware and routine features of the implementations described herein are shown and described. It will, of course, be understood that in the development of any such actual implementation, numerous implementation-specific decisions need to be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skills in the art having the benefit of this disclosure.

The embodiment(s) of the present invention includes a haptic system capable of generating mood-based haptic feedback and method for making the same. A haptic system includes a sensing device, a digital processing unit, and a haptic generator. The sensing device, in one embodiment, employs sensors to sense mood information indicating user's modalities and subsequently issues a sensing signal according to the user's modalities. Upon receipt of the sensing signal(s), the digital processing unit identifies a user's condition or mood. After generating a haptic signal according to the user's condition, a haptic generator generates haptic feedback in response to the haptic signal.

Figure 1:
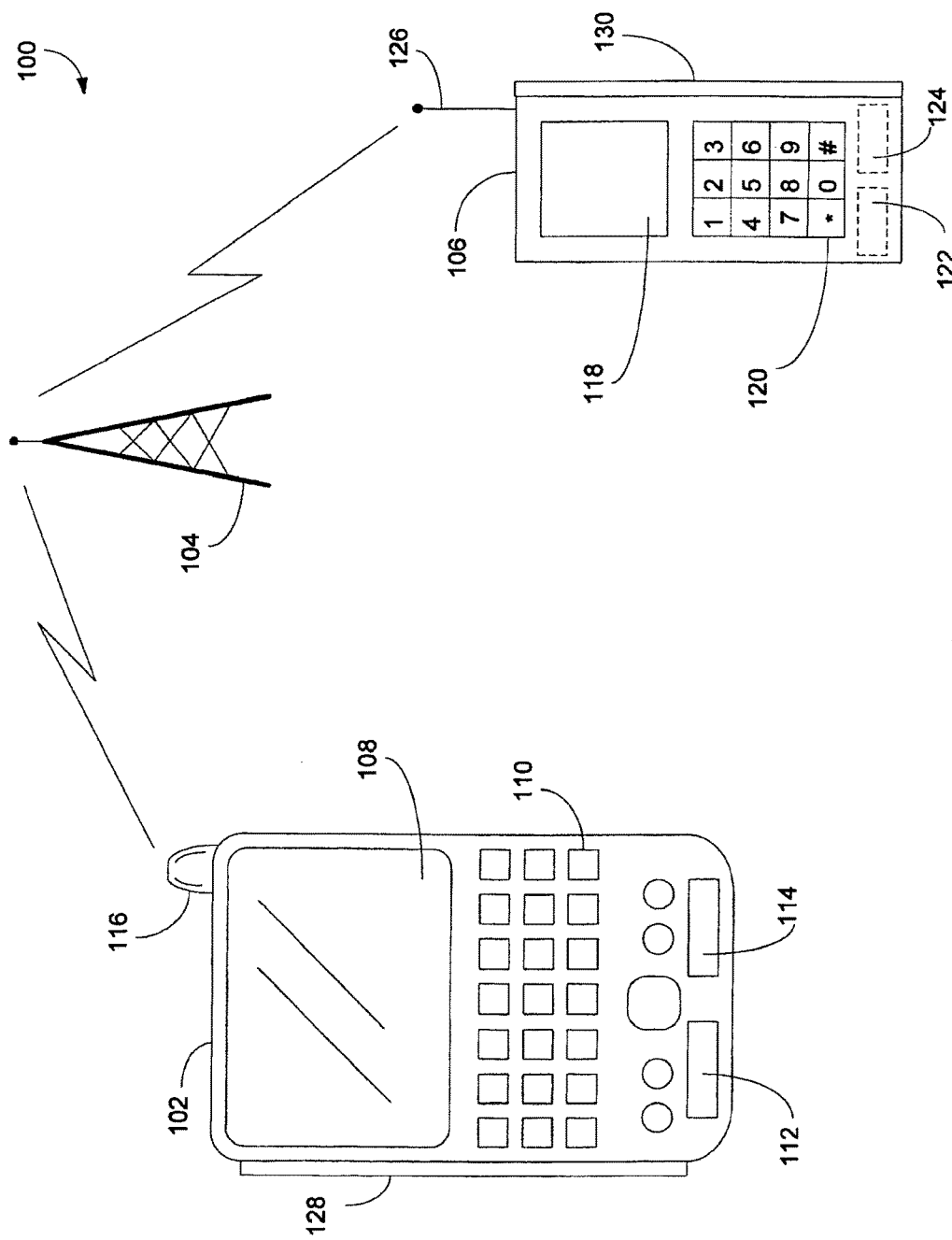
FIG. 1 is a diagram illustrating a haptic system capable of generating mood-based haptic sensation in accordance with one embodiment of the present invention.

FIG. 1 is a diagram 100 illustrating a haptic system capable of generating mood-based haptic sensation in accordance with one embodiment of the present invention. Diagram 100 includes a first portable device 102, a communications network 104, and a second portable device 106. In one embodiment, portable devices 102 and 106 can communicate with one another via network 104 which may include one or more communications networks, such as a wireless communications network, an Internet, a personal area network, a local area network, a metropolitan area network, a wide area network, and so forth. It should be noted that the underlying concept of the exemplary embodiment of the present invention would not change if additional blocks were added to or removed from diagram 100.

Portable device 102, in one embodiment, includes a mood-based haptic device 112, a sensing device 114, and a haptic generator 128. Additional components, such as a display 108, a keyboard 110, and an antenna 116, can be added to device 102. It should be noted that portable device 102 can be a mobile phone, a personal digital assistant ("PDA"), a cellular phone, a portable computer, a haptic watch, a haptic necklace, or the like. Portable device 106, on the other hand, includes a mood-based haptic device 122, a sensing device 124, and a haptic generator 130. Similarly, additional components, such as a display 118, a keyboard 120, and an antenna 126 may also be added to portable device 106. Portable device 102 and 106 may be the same or different devices, but they are capable of communicating with one another as long as they are both equipped with mood-based haptic devices.

Sensing device 114, in one embodiment, includes multiple sensors configured to sense and collect mood information relating to a user. For example, sensing device 114 employs sensors to detect and/or collect mood information via various modalities or user's mood states, which include, but not limited to, user's facial expressions, voice pitches, and/or user's biometrics. The biometrics, which is a subset of user's mood states, further include body temperature, body humidity or perspiration, heart pulse or rate, breathing rhythms, body posture, hand gestures or movements, and so forth. After obtaining the mood information, a digital processing unit, which could be onboard with portable device 102 or 106, identifies user's current mood and/or psychological condition(s) based on the collected mood information. The information relating to user's mood is subsequently forwarded to interested parties, who can be the user himself or herself or person(s) who is interacting with the user. For example, when two persons are talking over cellular phones, either party can sense the other person's mood over the mood-based haptic mechanism.

Sensing device 114, alternatively, also includes sensors to detect ambient conditions. For example, sensing device 114 collects ambient information relating to surroundings such as whether temperature, humidity, lighting, atmosphere pressure, and the like. Sensing device 114 and/or mood-based haptic device 112 can use ambient information together with the mood information to assess user's mood. It should be noted that ambient information can also indicate whether the user is in a hostile or friendly environment.

In an operation, user A, not shown in FIG. 1, uses portable device 102 talking and/or communicating with user B through portable device 106. Upon sensing user A's mood via sensing device 114, mood-based haptic device 112 sends the mood information of user A to portable device 106 via network 104. After receipt of the mood information, haptic generator 130 generates and sends a haptic feedback to user B indicating the mood of user A. Similarly, user A can also sense user B's mood via haptic generator 128 in the same or similar manner.

With the advent of advanced sensing technologies capable of detecting different aspects of human mood as well as environment conditions, artificial intelligence or computer assessment for human behaviors and/or psychological conditions with high-degree of accuracy is increasingly achievable. For example, sophisticated signal processing unit can process image, voice, and biometrics information to generate wealth of mood information or attributes to indicate mood or physical condition of a human or a user. Once the mood information is processed, haptic feedback is generated in view of the mood information, wherein the haptic feedback can be sent to the user, and/or to a community interacting with the user. Portable device 102 or 106 can be a hand held device, a wearable computer device, or other surrounding devices capable of identifying user's mood from various modalities. Portable device 102 is capable of providing mood-based haptic feedback to user(s) in the vicinity or over a remote location.

In one example, to sense a user's mood, a sensing technique for detecting facial expressions, voice analysis, and/or biometrics sensing can be employed. The sensing technique for instance can use a video camera to observe user's facial expressions. From certain facial expressions, user's emotional state can be deduced from video recordings. It should be noted that technology of analyzing facial images to infer human emotional state of mind has been matured and available. It should be further noted that video camera(s) is generally available with the device such as a camera on a phone or PDS.

The sensing technique may also employ various sound or audio sensors to record and/or facilitate voice analysis. It should be noted that voice frequency and voice intensity while talking on the phone may infer user's mood. For biometrics sensing, different sensors can be used to measure body temperature, humidity (or perspiration), breathing rhythm, and/or heart pulse to indicate user's mood or conditions. For example, a haptic wrist band or necklace can be used to sense the heat pulse as well as predicting the mood over time.

Depending on the applications, different modalities may be used to generate targeted mood-based haptic feedback. For example, to share a happy state of mind with a friend while talking over the phone, the communication can be augmented by sending from one user's phone to another with haptic cues signalizing the happy mood or pleasant state of mind. To capture user emotional state while dialing or talking on a cell phone, a digital camera or video camera on the cell phone, for instance, can be used to capture and then transmit captured mood information or facial expressions to the user being called.

Referring back to FIG. 1, the haptic system includes portable devices 102 and 106 wherein each portable device further includes one or more sensors and actuators. The sensors and actuators, in one aspect, can be constructed on the same device. Sensors are used to detect user conditions while actuators are used to provide haptic feedback in accordance with the user conditions. For example, a heart rate sensor is capable of sensing user's heart rate while a temperature sensor measures the user's body temperature. Detected information such as heart rate and body temperature are subsequently processed, and a series of haptic feedback are generated indicating current user's mood. It should be noted that the terms haptic feedback can be referred to as tactile effect, tactile feedback, haptic effect, force feedback, vibrotactile feedback, haptic cues, and so forth.

The mood-based haptic device can communicate between themselves via a wireless network 104. The wireless communications network may include local radio frequencies, Bluetooth, cellular (GPRS, CDMA, GSM, CDPD, 2.5G, 3G, etc.), Ultra-WideBand (UWB), WiMax, ZigBee, and/or other ad-hoc/mesh wireless network technologies. To reduce power consumption, device 102 or 106 can also use a relay station to amplify signal strength to conserve the power. For example, a relay station can receive haptic signals from other haptic device used by other users to conserve power and coverage.

Device 102 or 106 can also be used in individual or team sports such as poker players, swimmers in water polo, or cyclists on a tour to identify the mood condition of athlete. For example, device 102 may inform one of the cyclists to speed up or slow down to improve team performance in accordance with detected mood or psychological information. It should be noted that device 102 can also be used for other applications such as monitoring mentally unstable patients in a mental institution.

Haptic system, in one embodiment, can include multiple units wherein some of the units may be located in the chest, wrist, foot, and/or the like to sense user's mood. Haptic generator 128, for example, is capable of generating haptic cues or haptic warning signals at different levels of intensities for different levels of mood swings. For example, haptic generator 128 generates a minor haptic cue when the user is slightly unhappy, and generates an intensified haptic cue when the user is mad. It should be noted that using tactile feedback to indicate the user's physiological conditions can be a subtle, discreet, and non-intrusive communication method.

Sensing device 114 and haptic generator 128 can be combined or fabricated into a single device. For example, vibrotactile feedback or haptic feedback may be provided through a piezo material, shape memory alloy ("SMA"), eccentric rotating mass "ERM") or linear resonant actuator ("LRA"), or the like. Piezoelectric material, in one embodiment, may be used to perform both sensing functions and actuating function. Some haptic materials such as piezoelectric material have the physical property of sensing as well as providing vibrotactile effect. For example, piezoelectric material discharges a current indicating it detected a pressure when its physical shape deforms due to a pressure. The dimension of piezoelectric material can be reduced to a relatively small size such as 5 millimeters by 5 millimeters. Piezoelectric materials, in one embodiment, include crystals and/or ceramics such as quartz ($SiO_2$). When a voltage potential applies to the piezoelectric material, it deforms from its original shape to an expanded shape. Piezoelectric material may return to its original state as soon as the voltage potential is removed. Piezoelectric material, however, releases a current when it is being pressed. As a result, piezoelectric material can detect an input when it is being pressed. Similar functions of sensor/actuator may be performed if the piezoelectric material is replaced with other materials or devices, such as LRA, ERM, and SMA. SMA, in one example, is capable of maintaining its deformed shape for a period of time after the voltage potential is removed. It should be noted that the underlying concept of the embodiments of the present invention does not change if different materials other than piezoelectric actuators are employed.

An advantage of employing a mood-based haptic feedback is that it is essentially creating a communication channel to transmit mood information between the callers. The mood-based haptic system can be applied to variety of applications, such as conversations between multiple parties, team sports, military missions, interrogations, patient monitoring, and the like.

Figure 2:
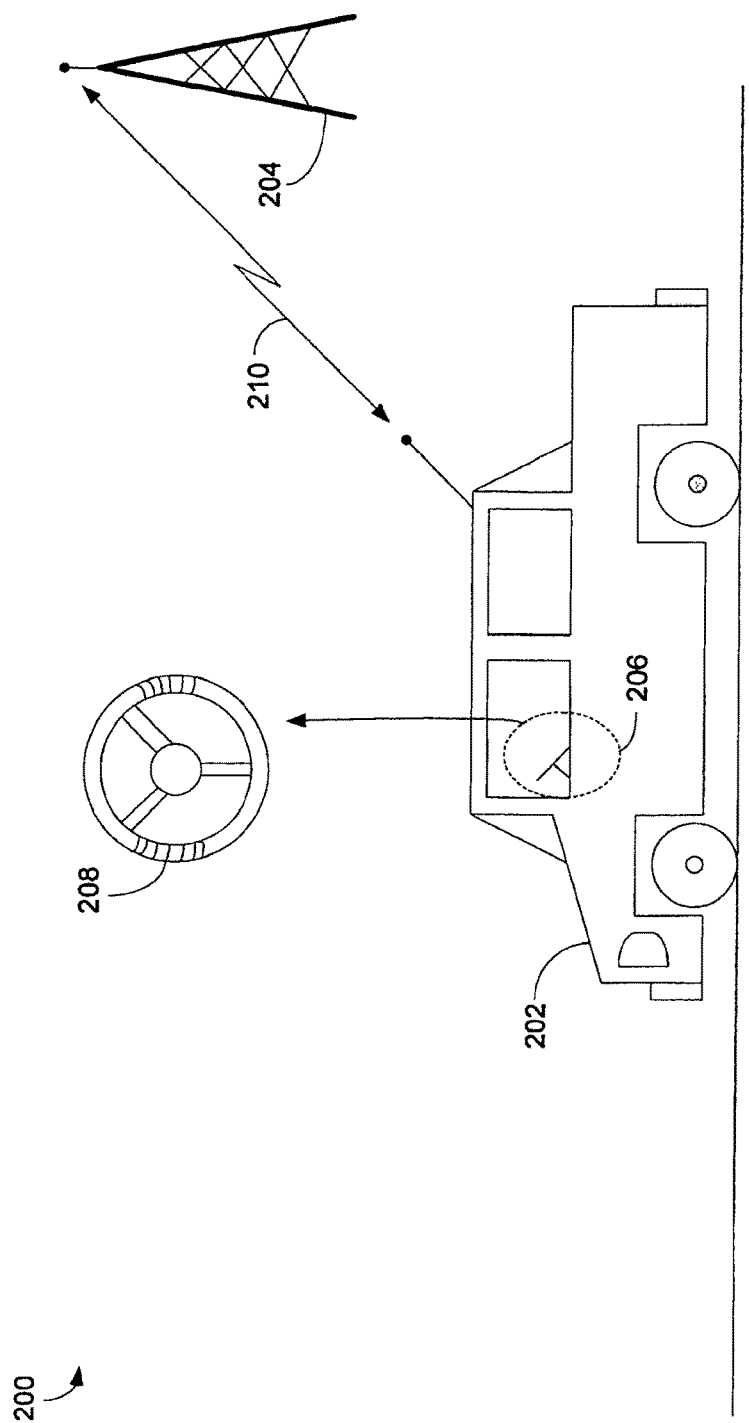
FIG. 2 is a diagram illustrating an exemplary application of an automobile environment having a mood-based haptic system in accordance with one embodiment of the present invention.

FIG. 2 is a diagram 200 illustrating an exemplary application of an automobile having a mood-based haptic system in accordance with one embodiment of the present invention. Diagram 200 includes an automobile 202 and a network 204, wherein automobile 202 further includes a steering wheel 206 having a mood-based haptic device 208. It should be noted that the underlying concept of the exemplary embodiment of the present invention would not change if additional devices and blocks were added to or removed from diagram 200.

Automobile 202, in one embodiment, includes a sensing device, a haptic generator, and a mood processing unit, not shown in FIG. 2, wherein the haptic generator can be incorporated with mood-based haptic device 208. Upon detecting the driver's mood condition, the haptic generator is capable of generating various haptic feedbacks to indicate driver's level of fatigue, alertness, distraction, and/or soberness. The haptic generator may vibrate the driver's seat to relieve driver's stress or to wake-up the driver. For example, wheel 206 generates vibrotactile feedback by activating mood-based haptic device 208 to remind the driver that he or she is too tired to continue operating the vehicle. Alternatively, the haptic generator can also broadcast driver's physical condition (or effectiveness) to interested parties, such as family members, company personal, highway patrol, and so forth. It should be noted that a similar mood-based haptic system can be applied to train, airline, and/or shipping industries.

During an operation, the sensing device of automobile 202 reads sensed inputs such as perspiration, facial expression, voice, heartbeat, et cetera from the driver. After processing sensed inputs, the mood processing unit deduces driver's state of mind, mood, feeling, et cetera in accordance with the sensed inputs. Upon identifying driver's mood condition, the haptic generator generates haptic feedback to indicate driver's present mood.

In one aspect, the mood-based haptic device 208 is configured to change the state of mind or mood (from sad to happy) of the same user. Moreover, device 208 can also be used to maintain user's current state of mind or mood (relaxation state, high concentration) of the same user by providing certain type of haptic feedback. Also, device 208 is capable of transmitting the same haptic effect to a third party individual or multiple individuals, such as a network group.

Figure 3:
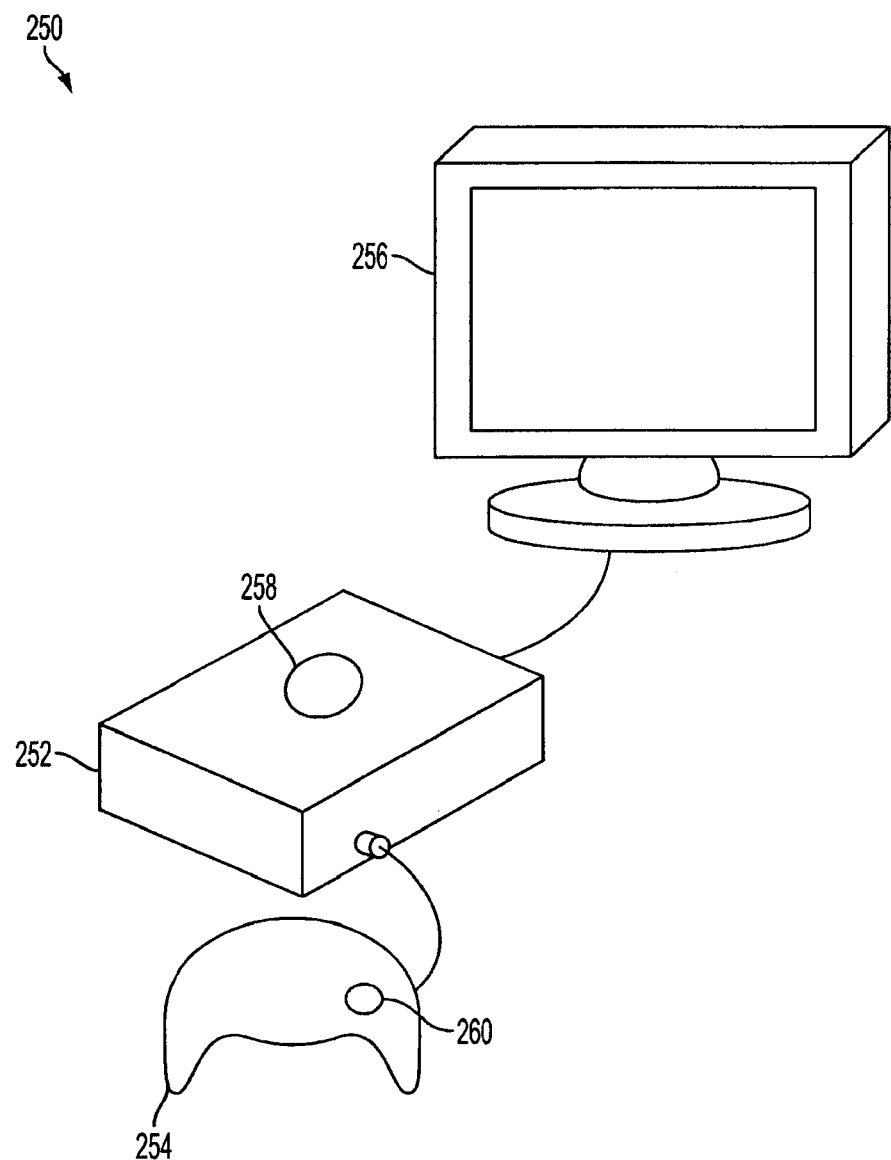
FIG. 3 is a diagram illustrating an exemplary application in a video game environment having a mood-based haptic system in accordance with one embodiment of the present invention.

FIG. 3 is a diagram 250 illustrating an exemplary application in a video game environment having a mood-based haptic system in accordance with one embodiment of the present invention. Diagram 250 includes a terminal 256, a game console 252, and a game controller 254, wherein the mood-based haptic controller 258-260 are placed in game console 252 and in controller 260. It should be noted that the underlying concept of the exemplary embodiment of the present invention would not change if additional devices or blocks were added to or removed from diagram 250.

For a gaming device, the game, in one embodiment, can adapt to a level of difficulty or environment depending on the mood or emotion of the player. For example, when the sensing device of mood-based haptic controller 258 or 260 senses a relaxed player (e.g. low humidity), the game console automatically increases the game to a more difficult level or a different game event. Alternatively, when sensing device of mood-based haptic controller 258 or 260 senses a tensed or excited mood (e.g. high humidity), the game console adjusts the game to an easier level or a different game event. In other words, the game console can monitor and determine how 'cool' the user is when he or she plays the game.

In an alternative embodiment, mood-based haptic system can also be used to enhance efficiency in work related environment or settings. For example, the speed of a manufacturing assembling line may be adjusted in accordance with workers' moods detected by the mood-based haptic system.

Figure 4:
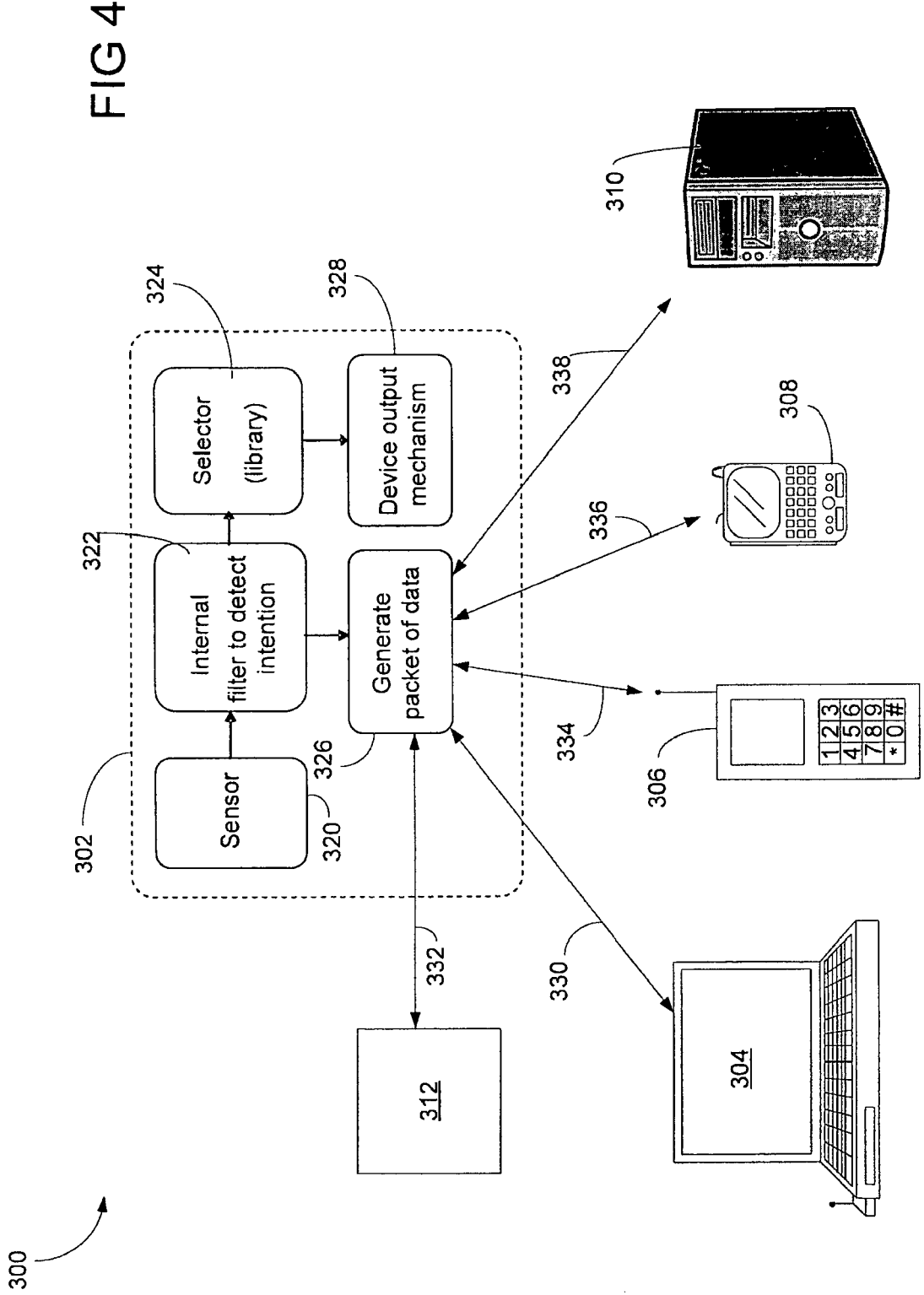
FIG. 4 illustrates a mood-based haptic system capable of communicating with other devices in accordance with one embodiment of the present invention.

FIG. 4 illustrates a mood-based haptic system capable of communicating with other devices in accordance with one embodiment of the present invention. Diagram 300 includes a portable or wearable interface device 302, a PC 304, a cellular phone 306, a PDA 308, a server 310, and a processing device 312, which is capable of executing instructions. It should be noted that the underlying concept of the exemplary embodiment of the present invention would not change if additional blocks such as power supply were added to or removed from diagram 300.

Device 302 further includes a sensor 320, an internal filter 322, a selector 324, a generator 326, and a haptic output device 328. In one embodiment, sensor 320 is configured to detect facial expressions, voice pitches, and biometrics in connection with the user of device 302. Filter 322 is used to filter any extraneous information such as unwanted images and voices, which are considered as natural and/or surrounding noises as oppose to mood information from the user. In another embodiment, internal filter 322 is located in a host computer, wherein the filtering process is implemented by a host processor. Generator 326 generates commands in response to the filtered mood information and transmits the input commands to one or more processing devices such as PC 304 or PDA 308 via various communication channels 332-338, which may be wired or wireless communications.

Selector 324 includes one or more haptic libraries used for storing haptic data containing a list of haptic effects. In one embodiment, the list of haptic effects is used to provide a haptic feedback to a user in accordance with the detected mood information. Each mood detection or input, for example, may require a unique haptic feedback. It should be noted that the library containing haptic data can also be located in a remote host computer. In an alternative embodiment, haptic data can be dynamically generated and continuously updated to emulate and/or reproduce detected mood state(s). To emulate mood state in real-time, selector 324 is capable of dynamically generating haptic effect to emulate detected mood and/or mood state(s). Haptic output device 328 generates haptic feedback in accordance with the haptic data from selector 324. For example, a vibration effect emulates a happy mood.

A function of device 302 is to communicate mood-based haptic feedback to one or more devices, such as laptop 304, cellular phone 306, PDA 308, server 310, and so on, at the same time. It should be noted that components 320-328 can also be distributed into several different entities depending on the applications. Device 302 can communicate with other devices 304-310 via cable connections, wireless connections, and a combination of wire and wireless networks.

Figure 5:
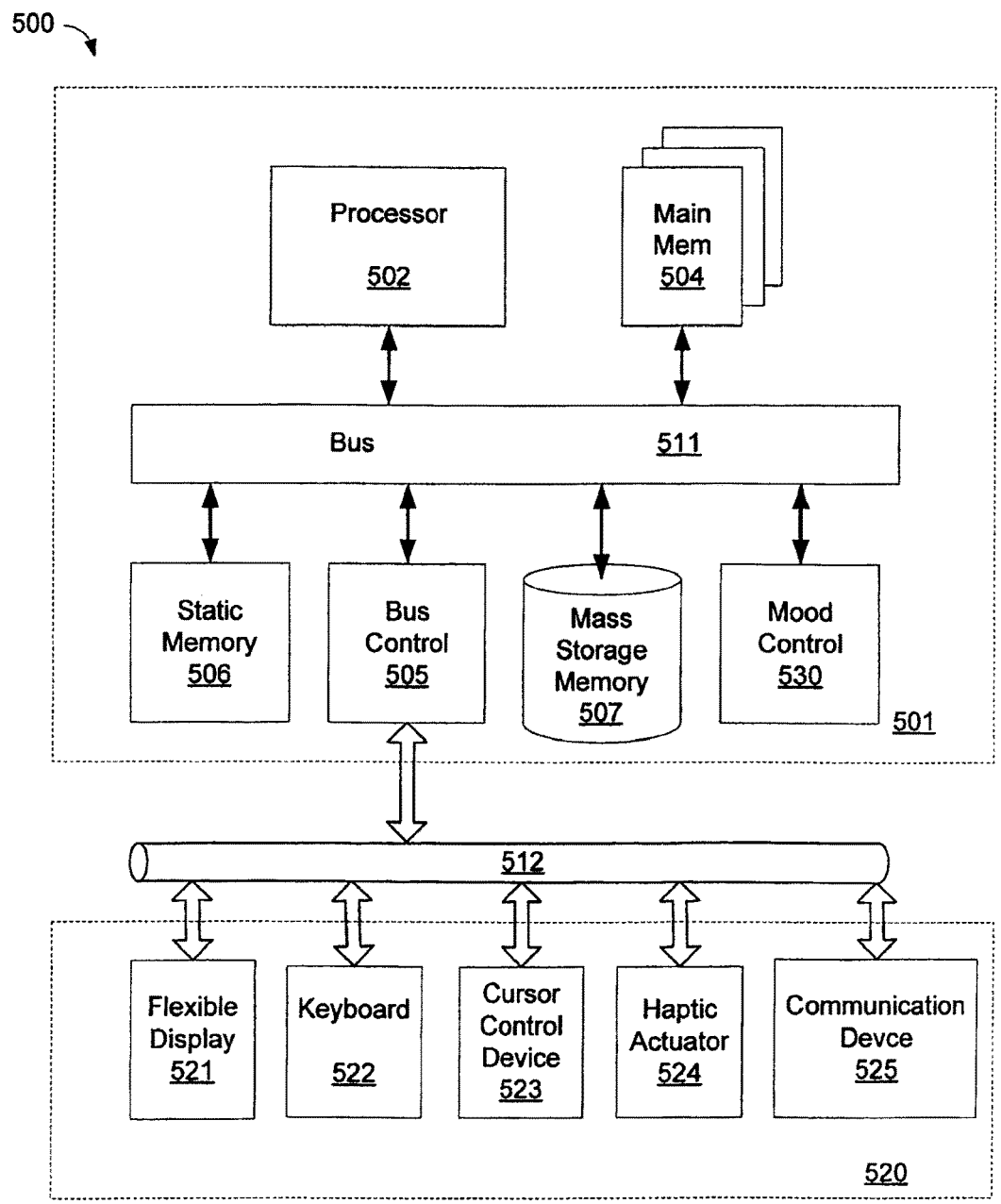
FIG. 5 illustrates a processing device capable of processing mood-based haptic information in accordance with one embodiment of the present invention.

FIG. 5 illustrates a processing unit 500 capable of processing mood-based haptic information in accordance with one embodiment of the present invention. Unit 500 includes a processing unit 501, an interface bus 511, and an input/output ("IO") unit 520. Processing unit 501 includes a processor 502, a main memory 504, a system bus 511, a static memory device 506, a bus control unit 505, a mass storage memory 507, and a mood control 530. Bus 511 is used to transmit information between various components and processor 502 for data processing. Processor 502 may be any of a wide variety of general-purpose processors or microprocessors, such as Pentium™ microprocessor, Intel® Core™2 Duo, Intel® Core™2 Quad, Intel® Xeon®, AMD Athlon™ processor, Motorola™ 68040, or Power PC™ microprocessor. Mood control 530 generates haptic feedback in response to mood-based input signals.

Main memory 504, which may include multiple levels of cache memories, stores frequently used data and instructions. Main memory 504 may be RAM (random access memory), MRAM (magnetic RAM), or flash memory. Static memory 506 may be a ROM (read-only memory), which is coupled to bus 511, for storing static information and/or instructions. Bus control unit 505 is coupled to buses 511-512 and controls which component, such as main memory 504 or processor 502, can use the bus. Bus control unit 505 manages the communications between bus 511 and bus 512. Mass storage memory 507, which may be a magnetic disk, an optical disk, hard disk drive, floppy disk, CD-ROM, and/or flash memories for storing large amounts of data. Actuator control module 530, in one embodiment, is an independent component (IC) that performs functions of haptic effect control. A function of actuator control 530 is to drive one or more haptic actuators 524, which could be a remote wearable ring. In another embodiment, actuator control module 530 may reside within processor 502, main memory 504, and/or static memory 506.

I/O unit 520, in one embodiment, includes a flexible display 521, keyboard 522, cursor control device 523, and communication device 525. Keyboard 522 may be a conventional alphanumeric input device for communicating information between processing unit 500 and computer operator(s). Another type of user input device is cursor control device 523, such as a conventional mouse, touch mouse, trackball, a finger or other type of cursor for communicating information between unit 500 and user(s). Communication device 525 is coupled to bus 512 for accessing information from remote computers or servers through wide-area network. Communication device 525 may include a modem or a wireless network interface device, or other similar devices that facilitate communication between unit 500 and the network.

The exemplary embodiment(s) of the present invention includes various processing steps, which will be described below. The steps of the embodiments may be embodied in machine or computer executable instructions. The instructions can be used to cause a general purpose or special purpose system which is programmed with the instructions to perform the steps of the embodiment(s) of the present invention. Alternatively, the steps of embodiment(s) of the present invention may be performed by specific hardware components that contain hard-wired logic for performing the steps, or by any combination of programmed computer components and custom hardware components.

Figure 6:
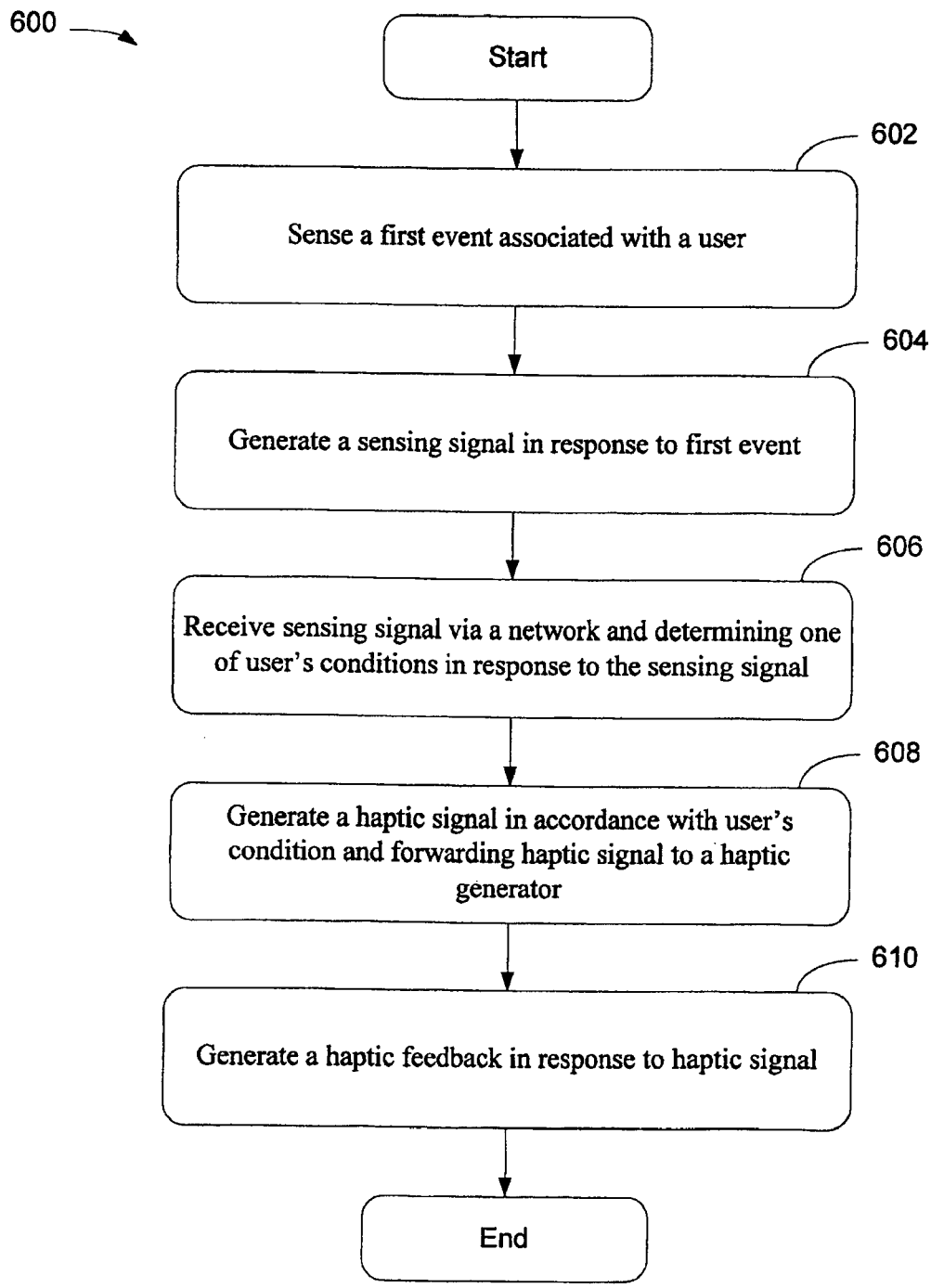
FIG. 6 is a flowchart illustrating a process of providing mood-based haptic feedback in accordance with one embodiment of the present invention.

FIG. 6 is a flowchart 600 illustrating a process of providing mood-based haptic feedback in accordance with one embodiment of the present invention. At block 602, a process capable of generating haptic feedback based on mood information senses a first event associated with a user. In one example, the process is configured to sense facial expressions, voices, and heart rates in connection to the user. In another example, the process can detect user's biometrics, such as body temperature and breathing rhythms.

At block 604, the process generates a sensing signal in response to the first event. In one embodiment, the process provides a happy indicator indicating the user's current mood when the first event indicates a happy mood. Alternatively, the process is capable of providing a sad indicator indicating user's current mood when the first event indicates a sad mood.

At block 606, the process receives the sensing signal via a network and subsequently, user's conditions or mood based on the sensing signal is determined. The process is also capable of obtaining the sensing signal through a wireless communications network. It should be noted that user's mood can be sampled continuously and user's mood can be updated accordingly.

At block 608, the process generates a haptic signal in accordance with the user's condition and forwarding the haptic signal to a haptic generator. In one embodiment, the process also sends the haptic signal to another haptic system operated by another user via a communications network.

At block 610, the process generates a haptic feedback in response to the haptic signal. In one embodiment, the process adjusts levels of difficulties of a game in accordance with the user's condition or mood. In another embodiment, the process provides an alert signal indicating the user's condition or mood. The process is, in one example, capable of sensing a second event associated with ambient condition. For instance, the process is capable of detecting temperature of a surrounding environment.

While particular embodiments of the present invention have been shown and described, it will be obvious to those of ordinary skills in the art that, based upon the teachings herein, changes and modifications may be made without departing from this invention and its broader aspects. Therefore, the appended claims are intended to encompass within their scope all such changes and modifications as are within the true spirit and scope of the exemplary embodiment(s) of is present invention.

What is claimed is:

1. A haptic system, comprising:
a sensing device, including at least one sensor, to sense mood information for a user of the haptic system;
a haptic generator to generate haptic feedback in accordance with a haptic signal, the haptic feedback being vibrotactile feedback that indicates at least one of a level of fatigue, a level of alertness, a level of distraction, or a level of sobriety;
a memory; and
a processor, coupled to the sensing device, the haptic generator and the memory, configured to:
receive the mood information from the sensing device,
identify a mood of the user from the mood information,
generate the haptic signal based on the mood, and
send the haptic signal to the haptic generator.

2. The haptic system according to claim 1, wherein the haptic generator is coupled to an automobile steering wheel.

3. The haptic system according to claim 1, wherein the haptic generator is coupled to an automobile seat.

4. The haptic system according to claim 1, further comprising a wireless communication device coupled to the processor, wherein the processor is further configured to determine a physical condition of the user based on the mood information, and transmit the physical condition to an interested party.

5. The haptic system according to claim 1, wherein the haptic generator is coupled to a game controller.

6. The haptic system according to claim 5, wherein the processor is further configured to:
execute a game; and
change a difficulty level of the game based on the mood.

7. The haptic system according to claim 1, wherein the mood information includes at least one of facial expressions, voice pitches or biometrics.

8. The haptic system according to claim 7, wherein the mood information is biometric information including at least one of a body temperature, a body humidity, a body perspiration, a heart pulse, a heart rate, a breathing rhythm, a body posture, a hand gesture or a hand movement.

9. A method of generating haptic effects for a haptic system, the method comprising:
receiving mood information for a user of the haptic system from a sensing device including at least one sensor;
identifying a mood of the user from the mood information;
generating a haptic signal based on the mood; and
sending the haptic signal to a haptic generator to generate haptic feedback in accordance with the haptic signal, the haptic feedback being vibrotactile feedback that indicates at least one of a level of fatigue, a level of alertness, a level of distraction, or a level of sobriety.

10. The method according to claim 9, wherein the haptic generator is coupled to an automobile steering wheel or an automobile seat.

11. The method according to claim 9, further comprising determining a physical condition of the user based on the mood information, and transmitting the physical condition to an interested party over a wireless network.

12. The method according to claim 9, further comprising:
executing a game; and
changing a difficulty level of the game based on the mood, wherein the haptic generator is coupled to a game controller.

13. The method according to claim 9, wherein the mood information includes at least one of facial expressions, voice pitches or biometrics.

14. The method according to claim 13, wherein the mood information is biometric information including at least one of a body temperature, a body humidity, a body perspiration, a heart pulse, a heart rate, a breathing rhythm, a body posture, a hand gesture or a hand movement.

15. A non-transitory computer-readable medium having instructions stored thereon that, when executed by a processor, cause the processor to generate haptic effects for a haptic system, the instructions comprising:
receiving mood information for a user of the haptic system from a sensing device including at least one sensor;

identifying a mood of the user from the mood information;

generating a haptic signal based on the mood; and sending the haptic signal to a haptic generator to generate haptic feedback in accordance with the haptic signal, the haptic feedback being vibrotactile feedback that indicates at least one of a level of fatigue, a level of alertness, a level of distraction, or a level of sobriety.

16. The non-transitory computer-readable medium according to claim 15, wherein the haptic generator is coupled to an automobile steering wheel or an automobile seat.

17. The non-transitory computer-readable medium according to claim 15, wherein the instructions further include determining a physical condition of the user based on the mood information, and transmitting the physical condition to an interested party over a wireless network.

18. The non-transitory computer-readable medium according to claim 15, wherein the haptic generator is coupled to a game controller, and wherein the instructions further include:

executing a game; and changing a difficulty level of the game based on the mood.

19. The non-transitory computer-readable medium according to claim 15, wherein the mood information includes at least one of facial expressions, voice pitches or biometrics.

20. The non-transitory computer-readable medium according to claim 15, wherein the mood information is biometric information including at least one of a body temperature, a body humidity, a body perspiration, a heart pulse, a heart rate, a breathing rhythm, a body posture, a hand gesture or a hand movement.

* * * * *